US012502175B2

(12) United States Patent
Xu et al.

(10) Patent No.: US 12,502,175 B2
(45) Date of Patent: Dec. 23, 2025

(54) SURGICAL STAPLING DEVICE WITH ANVIL TILT INDICATOR

(71) Applicant: Covidien LP, Mansfield, MA (US)

(72) Inventors: Yishuai Xu, Shanghai (CN); Xiliang Zhang, Shanghai (CN); Yanli Wan, Shanghai (CN); Yanjun Jiao, Shanghai (CN); Jinhang Liu, Shanghai (CN); Zhihua Zhang, Shanghai (CN); Xiucheng Shen, Shanghai (CN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/714,435

(22) PCT Filed: Dec. 2, 2021

(86) PCT No.: PCT/CN2021/135034

§ 371 (c)(1),
(2) Date: May 29, 2024

(87) PCT Pub. No.: WO2023/097597

PCT Pub. Date: Jun. 8, 2023

(65) Prior Publication Data

US 2025/0025176 A1 Jan. 23, 2025

(51) Int. Cl.
*A61B 17/115* (2006.01)
*A61B 90/00* (2016.01)
(Continued)

(52) U.S. Cl.
CPC .......... *A61B 17/1155* (2013.01); *A61B 90/08* (2016.02); *A61B 2017/00477* (2013.01);
(Continued)

(58) Field of Classification Search
CPC ............................ A61B 17/1155; A61B 90/08
See application file for complete search history.

(56) References Cited

U.S. PATENT DOCUMENTS 4,606,344 A 8/1986 Di Giovanni
5,350,104 A 9/1994 Main et al.
(Continued)

FOREIGN PATENT DOCUMENTS

CN 101534720 A 9/2009
CN 102186425 A 9/2011
(Continued)

OTHER PUBLICATIONS

International Search Report dated Jul. 28, 2022, issued in corresponding International Application No. PCT/CN2021/135034, 7 pages.

(Continued)

*Primary Examiner* — Nathaniel C Chukwurah

(57) ABSTRACT

A circular stapling device (10) includes a handle assembly (12) having an indicator assembly (80) that includes a clicker assembly (82) and a biasing member (84). The clicker assembly (82) provides an audible and/or tactile signal to a clinician when an anvil assembly (20) of the stapling device (10) is moved from a clamped position towards an open position a distance sufficient to allow an anvil head (56) of the anvil assembly (20) to pivot in relation to a reload assembly (18) of the stapling device (10) from an operative position to a tilted reduced profile position. The signal is provided to the clinician while the anvil assembly (20) is locked onto the stapling device (10).

16 Claims, 9 Drawing Sheets

(51) Int. Cl.
*A61B 17/00* (2006.01)
*A61B 17/11* (2006.01)
(52) U.S. Cl.
CPC ................. *A61B 2017/1103* (2013.01); *A61B 2090/0811* (2016.02)

(56) References Cited

U.S. PATENT DOCUMENTS

| | | | | |
|---|---|---|---|---|
| 2005/0023325 | A1* | 2/2005 | Gresham .............. | A61B 17/115 227/176.1 |
| 2006/0273135 | A1 | 12/2006 | Beetel | |
| 2008/0054045 | A1 | 3/2008 | Milliman et al. | |
| 2013/0284792 | A1* | 10/2013 | Ma ..................... | A61B 1/00087 227/176.1 |
| 2017/0348002 | A1* | 12/2017 | Murugesan ...... | A61B 17/07207 |
| 2020/0029969 | A1* | 1/2020 | Wang ................. | A61B 17/1155 |

FOREIGN PATENT DOCUMENTS

| | | | |
|---|---|---|---|
| CN | 107708579 | A | 2/2018 |
| CN | 108289683 | A | 7/2018 |
| CN | 110381853 | A | 10/2019 |

OTHER PUBLICATIONS

Written Opinion of the ISA dated Jul. 28, 2022, issued in corresponding International Application No. PCT/CN2021/135034, 4 pages.
Extended European Search Report for European Patent Application No. 21966029.7 mailed Jun. 2, 2025, 11 pages.

* cited by examiner

SURGICAL STAPLING DEVICE WITH ANVIL TILT INDICATOR

FIELD

This disclosure relates to stapling devices and, more particularly, to circular stapling devices having indicators for signaling to a clinician that the stapling device has moved towards an open position a distance to allow the anvil assembly to move to a tilted position.

BACKGROUND

Surgical stapling devices for suturing tissue are well known in the art and typically include a handle assembly, an adapter assembly, and an end effector supported on the adapter assembly for treating tissue. Such stapling devices are capable of suturing tissue more quickly than traditional suturing techniques to reduce time required to perform surgical procedures and thus reduce trauma to a patient. Typically, surgical stapling devices are designed to simultaneously cut and seal tissue.

Circular surgical stapling devices generally include an annular cartridge assembly that supports a plurality of annular rows of fasteners, and an annular anvil assembly that is operatively associated with the cartridge assembly to provide a surface against which the fasteners are formed upon a firing of the circular stapling device. The anvil assembly is movable in relation to the cartridge assembly between open and clamped positions and includes a center rod and an anvil head that is pivotably supported on a distal portion of the center rod such that the anvil head is movable from an operative position to a tilted, low-profile position. The center rod is configured to be releasably coupled to an anvil retainer of the circular stapling device to facilitate delivery of the anvil assembly to a surgical site independently of the circular stapling device. To lock the anvil head to the anvil center rod, the anvil assembly is moved from its open position towards its clamped position.

After a surgical procedure is completed, the anvil assembly needs to be moved from the clamped position towards the open position to provide spacing between the anvil head and the cartridge assembly to allow the anvil head to move to the tilted position. However, the anvil assembly should remain locked to the anvil retainer to prevent separation of the anvil assembly from the anvil retainer during removal of the circular stapling device from the surgical site.

A continuing need exists in the art for a circular stapling device that signals a clinician when the anvil assembly is in a position in which the anvil head is tilted and locked to the anvil retainer.

SUMMARY

This disclosure is directed to a circular stapling device including a handle assembly having an indicator assembly, an elongate body, and a tool assembly that includes a reload assembly and an anvil assembly. The anvil assembly includes a center rod and an anvil head that is supported on the center rod for movement between an operative position and a tilted reduced profile position. The anvil assembly is supported on an approximation mechanism and is movable between open and clamped positions in relation to the reload assembly. The anvil assembly locks onto the approximation mechanism when the anvil assembly is located between the open and clamped positions. The indicator assembly includes a clicker assembly that provides an audible and/or tactile signal to a clinician when the anvil assembly is moved from the clamped position towards the open position a distance sufficient to allow the anvil head to pivot from the operative position to the tilted reduced profile position. The signal is produced by the indicator assembly while the anvil assembly is locked onto the approximation mechanism.

Aspects of the disclosure are directed to a circular stapling device including a handle assembly, an elongate body, a tool assembly, and an approximation member. The handle assembly includes a housing, a firing trigger, and an indicator assembly. The indicator assembly includes a clicker assembly. The elongate body has a proximal portion coupled to the handle assembly and a distal portion. The tool assembly is coupled to the distal portion of the elongate body and includes a reload assembly and an anvil assembly. The anvil assembly has a center rod and an anvil head that is coupled to the center rod for movement between an operative position and a tilted reduced profile position. The approximation mechanism includes a rotation knob, a drive screw, and an anvil retainer. The rotation knob is rotatably supported on the housing of the handle assembly and is coupled to the anvil retainer via the drive screw. The anvil retainer extends from the reload assembly and is adapted to be releasably coupled to the center rod of the anvil assembly. The approximation mechanism is operable to move the anvil assembly in relation to the reload assembly between open and clamped positions. The clicker assembly is operably associated with the approximation mechanism and is movable in response to operation of the approximation mechanism to provide an audible signal to a clinician that the anvil assembly is positioned between the open and clamped positions and spaced from the reload assembly a distance to allow movement of the anvil head from the operative position to the tilted position.

In some aspects of the disclosure, the approximation assembly includes a screw stop that is supported on the drive screw within the housing of the handle assembly.

In certain aspects of the disclosure, the screw stop is movable within the housing between advanced and retracted positions into engagement with the clicker assembly in response to operation of the approximation mechanism to provide the audible signal to a clinician.

In aspects of the disclosure, the clicker assembly includes a clicker that is movable between a proximal position and a distal position in response to movement of the screw stop from its retracted position towards its advanced position to provide the audible signal to a clinician.

In some aspects of the disclosure, the clicker includes an abutment member, and the housing of the handle assembly supports an engagement surface.

In certain aspects of the disclosure, the abutment member is movable into engagement with the engagement surface when the clicker moves from its distal position towards its proximal position to provide the audible signal to a clinician.

In aspects of the disclosure, the indicator assembly includes a biasing member that is positioned to urge the clicker assembly towards its proximal position.

In some aspects of the disclosure, the clicker assembly includes a clicker that supports a boss and the housing of the handle assembly defines a cam slot that receives the boss.

In certain aspects of the disclosure, the cam slot is configured to pivot the clicker from a first position aligned with the screw stop to a second position misaligned with the screw stop in response to movement of the screw stop from its retracted position towards its advanced position.

In aspects of the disclosure, the clicker assembly includes a restrictor that is movable from a first position spaced from the screw stop to a second position engaged with the screw stop to increase resistance to movement of the screw stop within the housing of the handle assembly.

In some aspects of the disclosure, the increased resistance provides a tactile signal to a clinician that the anvil assembly is spaced from the reload assembly a distance to allow movement of the anvil head from the operative position to the tilted position.

In certain aspects of the disclosure, the clicker defines a channel, and the restrictor is movable within the channel from the first position to the second position.

In aspects of the disclosure, the clicker assembly includes a first biasing member that is positioned to urge the restrictor towards its second position.

In some aspects of the disclosure, the clicker assembly includes a retention member that engages the restrictor to retain the restrictor in its first position.

In certain aspects of the disclosure, the clicker assembly includes a second biasing member that is positioned to urge the retention member into engagement with the restrictor.

In aspects of the disclosure, the channel includes a vertical portion and a horizontal portion, and the restrictor is received within the vertical portion and the retention member is received within the horizontal portion.

Other aspects of the disclosure are directed to a handle assembly that includes a housing, an approximation mechanism, and in indicator assembly. The housing defines a cavity and has an engagement surface. The approximation mechanism includes a rotation knob, a drive screw, and a screw stop supported within the housing on the drive screw. The screw stop is movable between advanced and retracted positions within the housing in response to operation of the rotatable member. The indicator assembly is supported within the cavity of the housing and has a clicker assembly that includes a clicker that is movable between a proximal position and a distal position. The clicker has an abutment member that is movable with the clicker from the distal position to the proximal position into engagement with the engagement surface of the housing in response to movement of the screw stop from its retracted position towards its advanced position to produce an audible signal.

Other aspects, features, and advantages will be apparent from the description, the drawings, and the claims that follow.

BRIEF DESCRIPTION OF DRAWINGS

Various aspects of the disclosure are described herein below with reference to the drawings, wherein.

DETAILED DESCRIPTION

Figure 1:
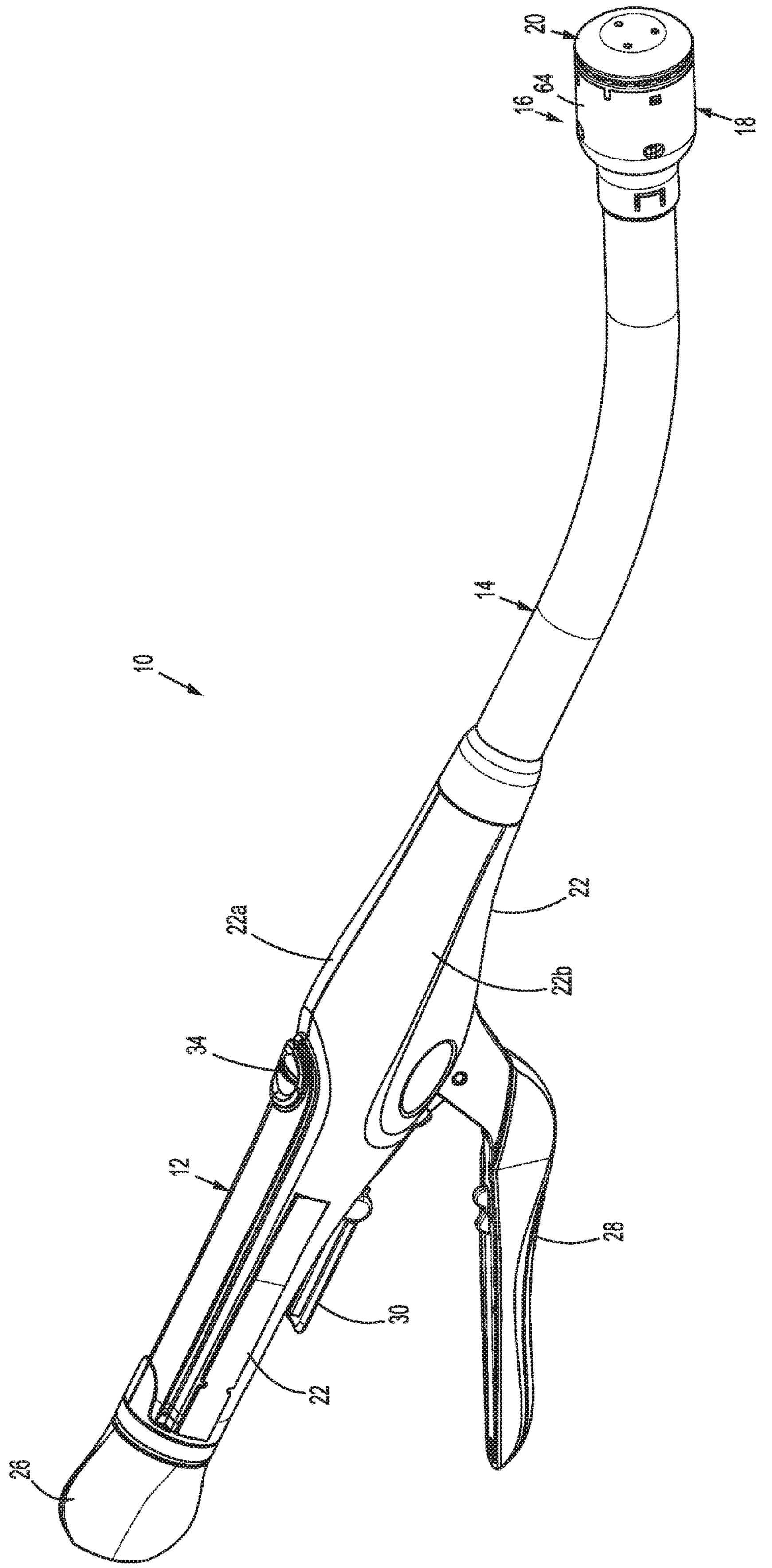
FIG. 1 is a side perspective view of a circular stapling device according to aspects of this disclosure with an anvil assembly in a clamped position.

The disclosed surgical stapling device will now be described in detail with reference to the drawings in which like reference numerals designate identical or corresponding elements in each of the several views. However, it is to be understood that the aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician during use of the device in its customary fashion, while the term "distal" is used generally to refer to that portion of the device that is farther from the clinician during use of the device in its customary fashion. In addition, the term "clinician" is used generally to refer to medical personnel including doctors, nurses, and support personnel. Further, directional terms such as front, rear, upper, lower, top, bottom, distal, proximal, and similar terms are used to assist in understanding the description and are not intended to limit the disclosure.

A circular stapling device is disclosed that includes a handle assembly having an indicator assembly, an elongate body, and a tool assembly including an anvil assembly and a reload assembly. The anvil assembly includes a center rod and an anvil head that is supported on the center rod for pivoting movement between an operative position and a tilted, reduced profile position. The stapling device has an approximation mechanism that facilitates movement of the anvil assembly in relation to the reload assembly between open and clamped positions. The approximation mechanism includes an anvil retainer that extends from the elongate body through the reload assembly. The center rod of the anvil assembly is releasably coupled to the anvil retainer. The anvil retainer and the center rod are withdrawn into the reload assembly when the anvil assembly is moved towards the clamped position to lock the anvil assembly to the center rod. The indicator assembly is associated with the approximation mechanism. After the stapling device is fired and the anvil assembly is moving from the clamped position towards the open position, while the anvil assembly is locked to the anvil retainer, the indicator assembly provides an audible and/or a tactile signal to a clinician that the anvil head has reached a position spaced from the reload assembly a sufficient distance for the anvil head to tilt to the reduced profile position.

FIG. 1 illustrates a circular stapling device shown generally as stapling device 10 which includes a handle assembly 12, an elongate body 14, and a tool assembly 16. The tool assembly 16 includes a cartridge or reload assembly 18 and an anvil assembly 20. In aspects of the disclosure, the reload assembly 18 is releasably coupled to a distal portion of the elongate body 14. Alternately, the reload assembly 18 can be fixedly coupled to the distal portion of the elongate body 14.

Figure 3:
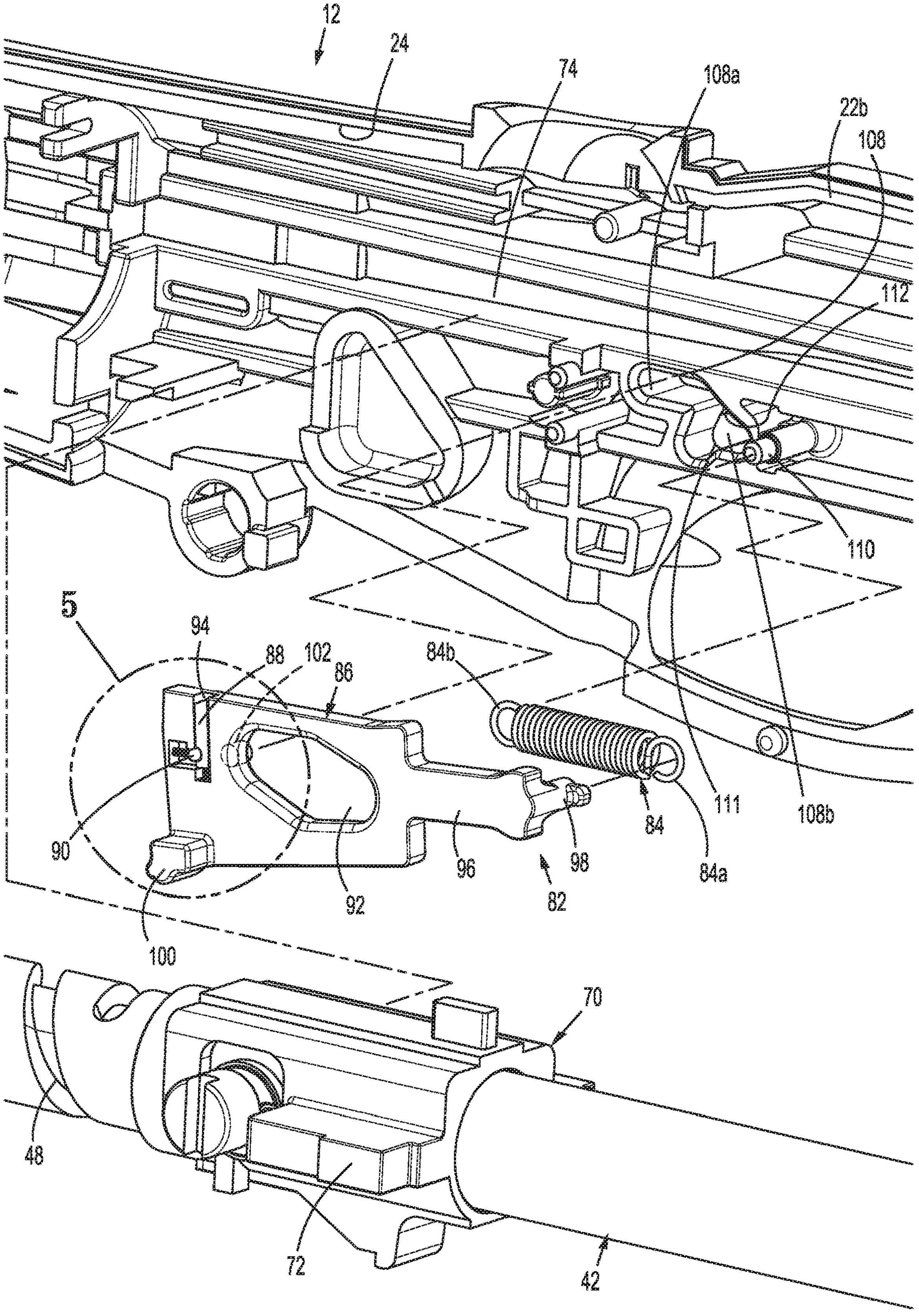
FIG. 3 is an exploded side perspective view of the portion of the handle assembly shown in FIG. 2.
Figure 4:
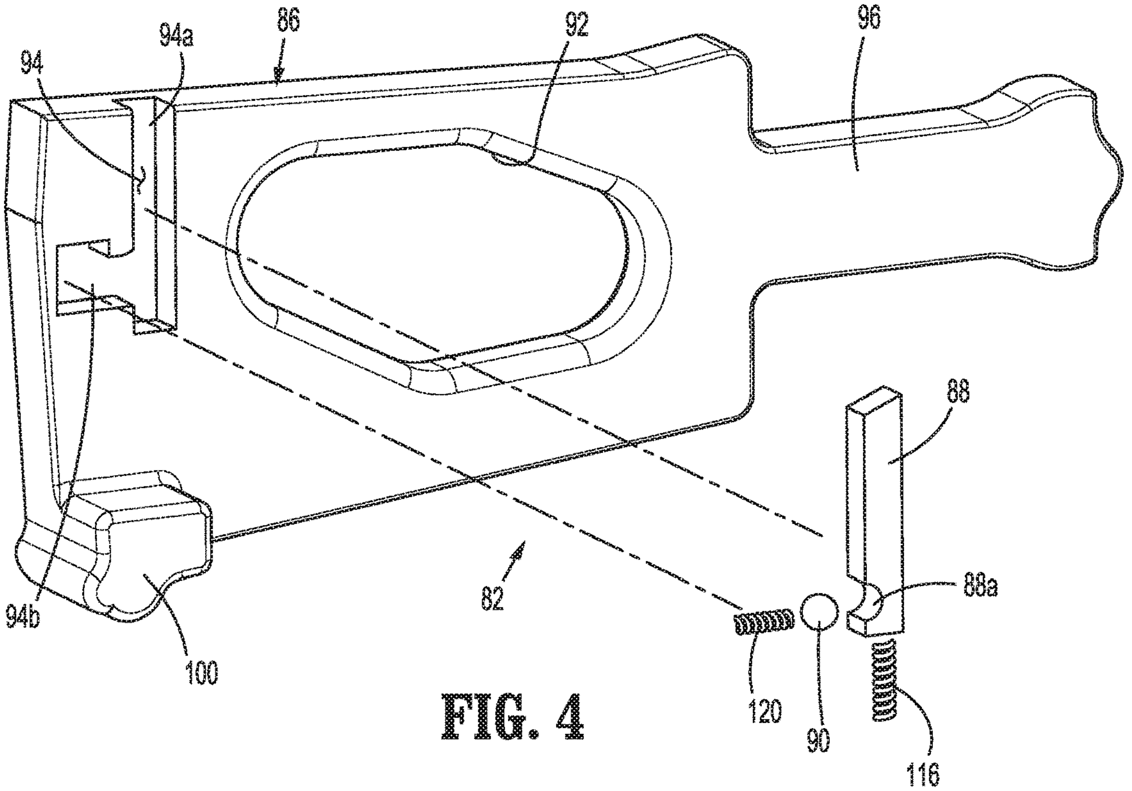
FIG. 4 is an exploded view of an indicator assembly of the circular stapling device shown in FIG. 1.
Figure 5:
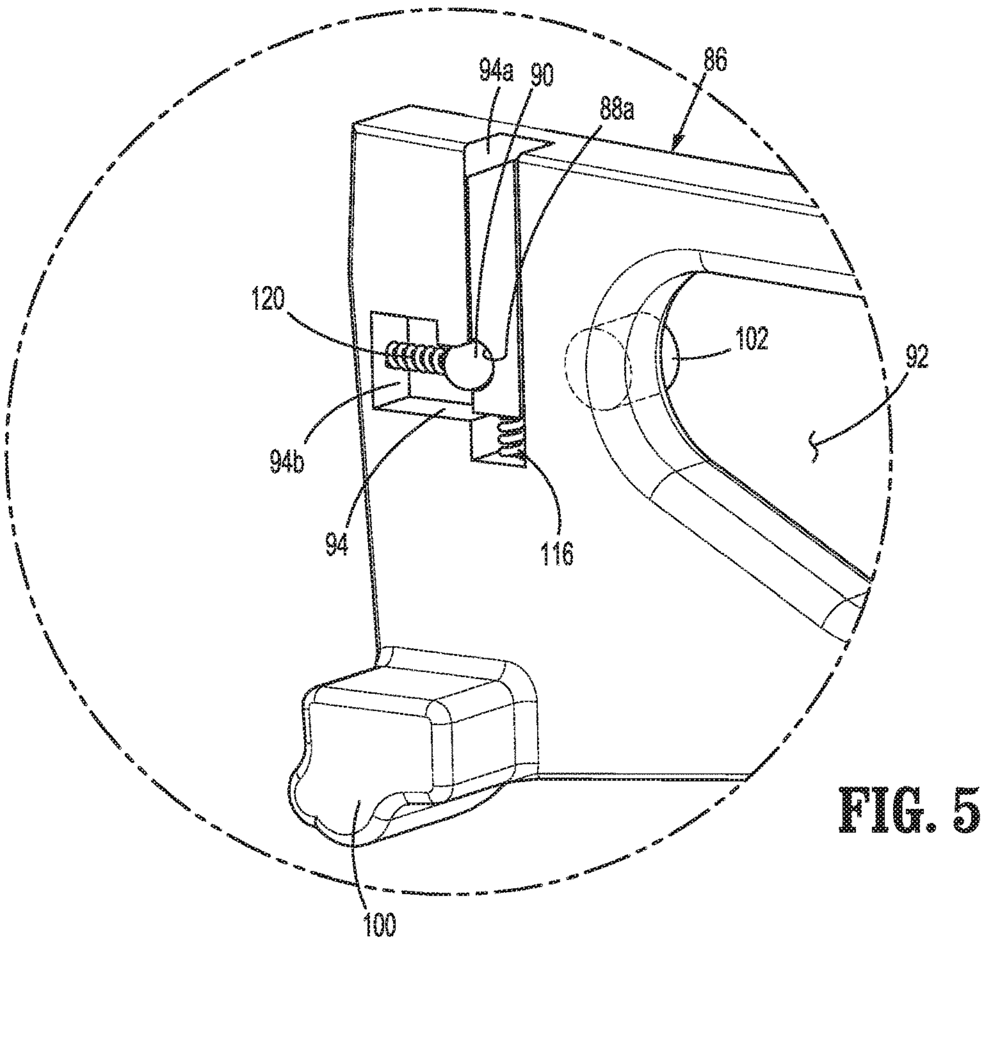
FIG. 5 is an enlarged view of the indicated area of detail shown in FIG. 3.

The handle assembly 12 has a grip portion or housing 22 that defines a cavity 24 (FIG. 3) that receives internal components of the handle assembly 12 that are described in further detail below. In aspects of the disclosure, the housing 22 includes half-sections 22*a* and 22*b* that are coupled together to define the cavity 24 and supports a rotation knob 26, a firing trigger 28, and a lockout member 30. The rotation knob 26 forms part of an approximation mechanism 32 (FIG. 1A) that is coupled to the anvil assembly 20 and can be actuated to move the anvil assembly 20 in relation to the reload assembly 18 between an open position and a clamped position (FIG. 1). The firing trigger 28 is supported on the housing 22 and can be actuated to eject staples from the reload assembly 18. The lockout member 30 is supported on the housing 18 and is movable from a locked position in which the lockout member 30 prevents actuation of the firing trigger 18 to an unlocked position (FIG. 1) in which the lockout member 30 permits actuation of the firing trigger 18. The handle assembly 12 also includes an indicator mechanism 34 that provides a signal to a clinician when the stapling device 10 is in a fire-ready position. For a more detailed description of the internal components of the handle assembly 12 of the stapling device 10, see, U.S. Pat. No. 6,945,444 (hereinafter "the '444 patent").

Figure 1A:
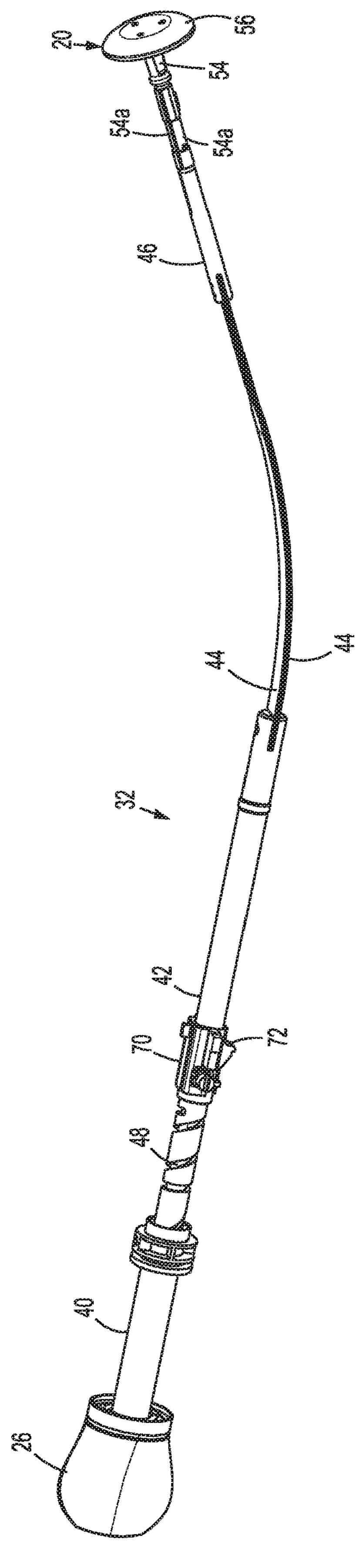
FIG. 1A is a side perspective view of an approximation mechanism of the circular stapling device shown in FIG. 1 with the anvil assembly coupled to an anvil retainer of the approximation mechanism.
Figure 2:
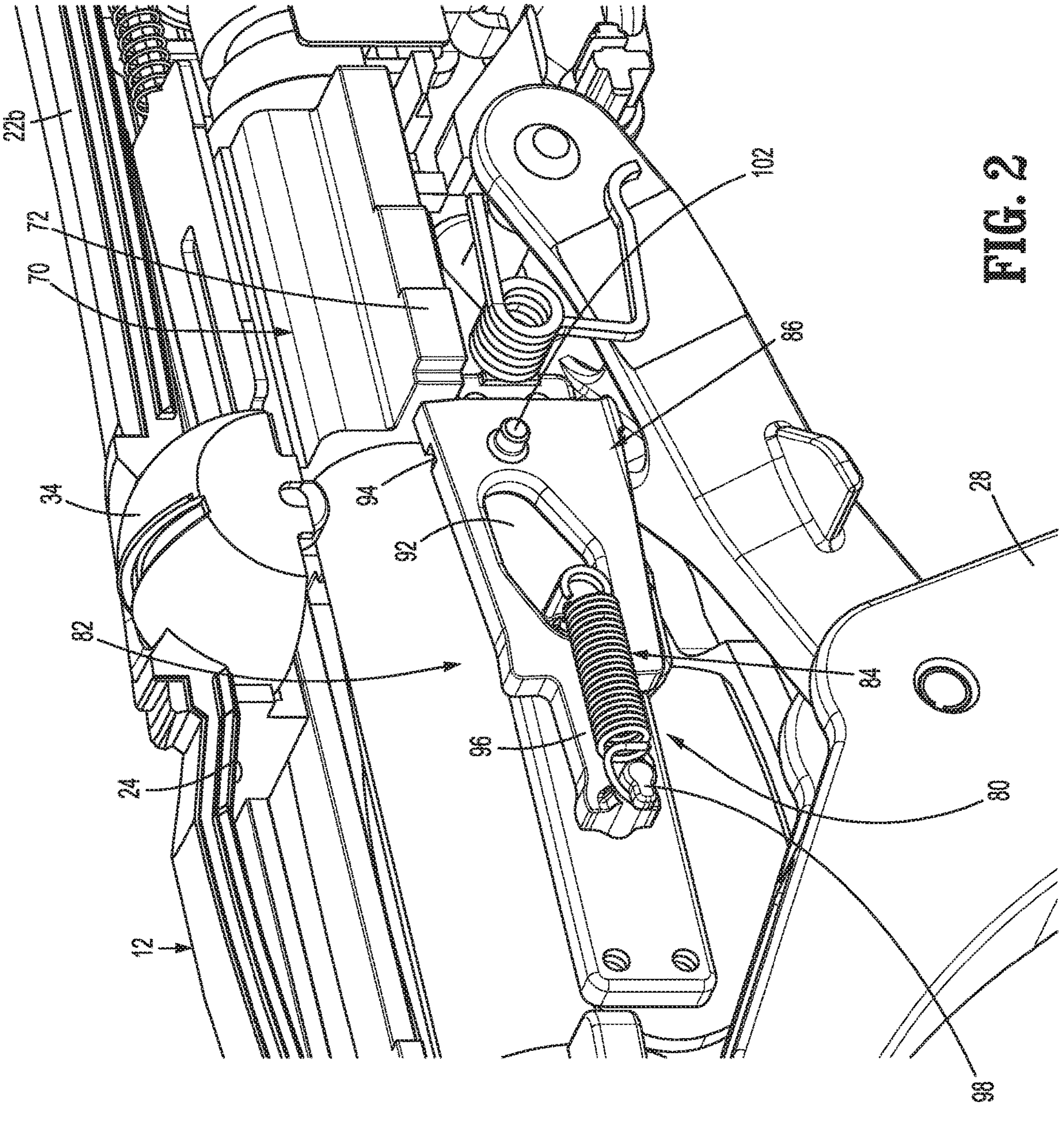
FIG. 2 is a side perspective cutaway view of a portion of a handle assembly of the circular stapling device shown in FIG. 1 with a portion of a housing of the handle assembly removed.

FIG. 1A illustrates the approximation mechanism 32 of the stapling device 10 (FIG. 1) which includes the rotation knob 26, a sleeve 40, a drive member, e.g., drive screw 42, one or more extensions 44, and an anvil retainer 46. The rotation knob 26 is secured to the sleeve 40 and is rotatable to cause rotation of the sleeve 40. The sleeve 40 is axially fixed to the housing of the handle assembly 12 and receives a proximal portion of the drive screw 42. The sleeve 40 supports a cam member (not shown) that extends inwardly from the sleeve 40 towards the drive screw 42. The proximal portion of the drive screw 42 defines a helical channel 48 that receives the cam member of the sleeve 40 such that rotation of the sleeve 40 causes axial movement of the drive screw 42.

Figure 10:
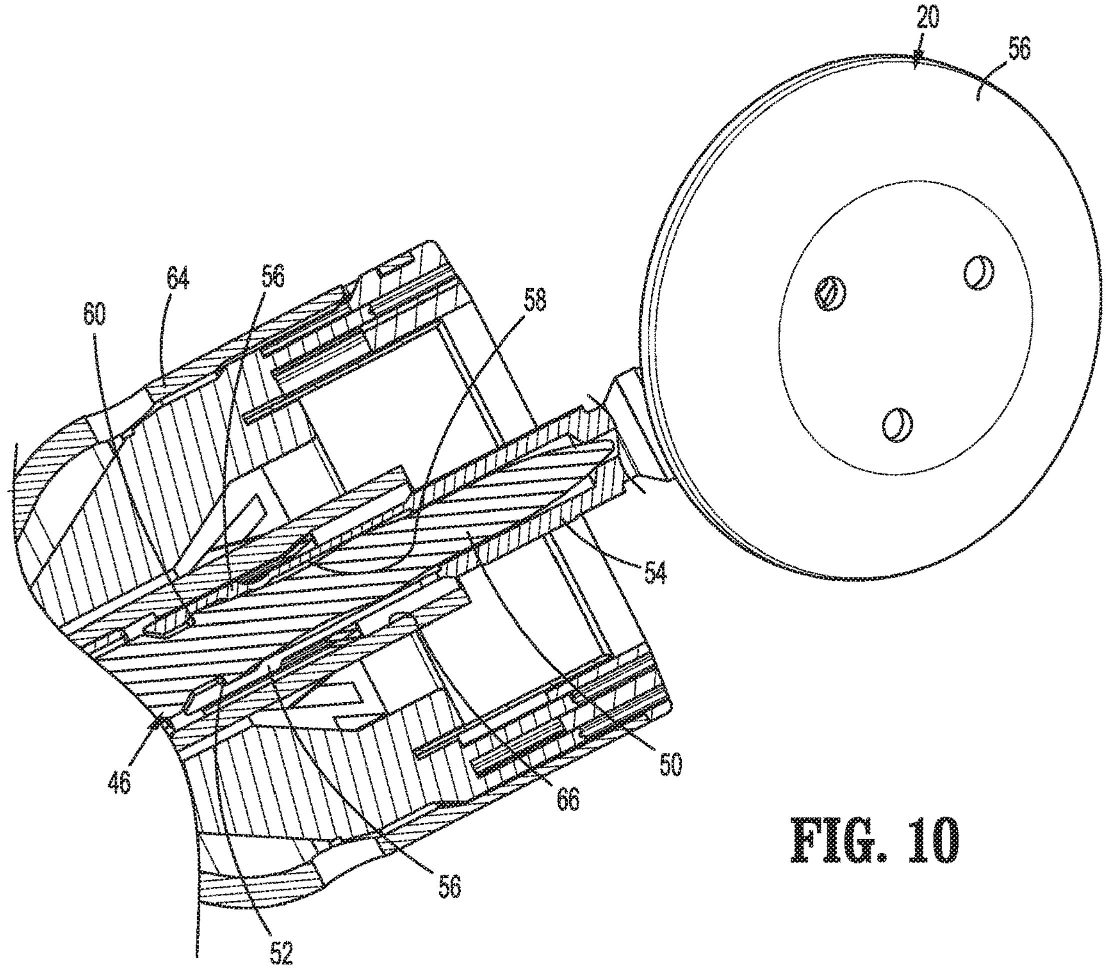
FIG. 10 is a side perspective view of a distal portion of the circular stapling device shown in FIG. 1 with the anvil assembly in a position between the open and clamped positions locked to the anvil retainer and tilted.

The extensions 44 have proximal portions that are secured to a distal portion of the drive screw 42 and distal portions that are secured to the anvil retainer 46. The extensions 44 extend from the drive screw 42 distally through the elongate body 14. In aspects of the disclosure, the extensions 44 include flexible bands that are supported adjacent one another and are pinned to the drive screw 42 and to the anvil retainer 46 such that axial movement of the drive screw 42 causes axial movement of the extensions 44 and the anvil retainer 46. In certain aspects of the disclosure, the anvil retainer 46 has a distal portion that defines a trocar portion 50 and a central portion that includes an annular retention member 52 (FIG. 10).

The anvil assembly 20 includes a center rod 54 and an anvil head 56. The anvil head 56 is pivotably coupled to the center rod 54 and is pivotable from an operative position (FIG. 1) to a tilted, reduced profile position (FIG. 10). The center rod 54 includes a plurality of resilient legs 54*a* that define a channel 58 (FIG. 10) that receives the trocar portion 50 of the anvil retainer 46 when the anvil assembly 20 is coupled to the anvil retainer 46. Each of the resilient legs 54*a* includes an inwardly extending engagement surface 60 (FIG. 10) that engages the annular retention member 52 of the anvil retainer 46 to couple the anvil assembly 20 to the anvil retainer 46 of the approximation mechanism 32.

The reload assembly 18 includes a housing 64 that defines a central though bore 66 (FIG. 10) that receives the anvil retainer 46 and the center rod 54 when the anvil assembly 20 is moved from the open position towards the clamped position (FIG. 1). When the resilient legs 54*a* of the center rod 54 are received within the central through bore 66 of the housing 64 of the reload assembly 18, the resilient legs 56 of the center rod 54 are prevented from flexing outwardly and the anvil assembly 20 is locked onto the anvil retainer 46. When the anvil assembly 20 is in the open position or near the open position spaced from the reload assembly 18, the resilient legs 54*a* of the center rod 54 are positioned distally of the central through bore 66 of the housing 64 of the reload assembly 18 such that the resilient legs 54*a* of the center rod 54 will flex outwardly upon application of a force in the distal direction on the anvil assembly 20 to release or disengage the anvil assembly 20 from the anvil retainer 46.

As described above, the anvil head 56 of the anvil assembly 20 can pivot in relation to the center rod 54 from an operative position to a tilted, reduced profile position. For a more detailed description of the operation of the tiltable anvil head of the anvil assembly 20, see the '444 patent. The anvil head 56 is moved to the reduced profile position to allow for easier removal of the anvil assembly 20 from a body lumen. For the anvil head 56 of the anvil assembly 20 to pivot to the reduced profile position, the anvil assembly 20 must be spaced from the reload assembly 18 by a distance equal to about half the diameter of the anvil head 56 such that pivotable movement of the anvil head 56 is unobstructed by the reload assembly 18.

The approximation mechanism 32 includes a screw stop 70 (FIG. 1A) that is fixedly supported on the drive screw 42 and includes radially extending wings 72 that are received within channels 74 (FIG. 3) defined within the housing 22 of the handle assembly 12 of the stapling device 10 (FIG. 1). The screw stop 70 engages inner surfaces of the housing 64 of the handle assembly 18 in the retracted and advanced positions of the approximation mechanism 32 to define the open and clamped positions of the anvil assembly 20. For a more detailed description of the configuration and function of the screw stop 70, see the '444 patent.

FIGS. 2-6 illustrate an indicator assembly 80 of the handle assembly 12 of the stapling device 10 (FIG. 1). The indicator assembly 80 includes a clicker assembly 82 and a biasing member 84. The clicker assembly 82 includes a clicker 86, a restrictor 88, and a retention member 90. The clicker 86 includes a body 86*a* that defines a central opening 92 and a channel 94 and includes a distally extending finger 96, a spring coupling member 98 (FIG. 3), an abutment member 100, and a boss 102.

The clicker 86 is supported within the housing 18 of the handle assembly 12. More specifically, the finger 96 of the clicker 86 is received within a channel 106 (FIG. 6) of the housing 18 of the handle assembly 12 and the boss 102 is received within a cam slot 108 defined within the housing 18 of the handle assembly 12. The finger 96 has a distal portion that includes arcuate surfaces 96*a* (FIG. 6) that allow the distal portion of the finger 96 of the clicker 86 to pivot within the housing 18 of the handle assembly 12. The spring coupling member 98 is formed on a distal end of the finger 96 and is coupled to one end 84*a* of the biasing member 84. The other end 84*b* of the biasing member 84 is coupled to a post 110 that is secured to the housing 18 of the handle assembly 12 such that the biasing member 84 urges the clicker 86 proximally within the housing 18 of the handle assembly 12. In some aspects of the disclosure, the biasing member 84 includes a coil spring although the use of other biasing member types is envisioned.

The cam slot 108 in the housing 18 of the handle assembly 12 includes a proximal portion 108*a* and a distal portion 108*b*. The proximal portion 108*a* of the cam slot 108 is substantially linear and horizontal as viewed in FIG. 6, and the distal portion of the cam slot 108 defines a cavity 111 and includes a cam surface 112 that is angled downwardly from the proximal portion 108*a* of the cam slot 108 in a distal direction.

The channel 94 defined in the clicker 86 has a backward L-shaped configuration and includes a vertical portion 94*a* (as viewed in FIG. 7) that receives the restrictor 88 and a horizontal portion 94*b* that receives the retention member 90. The vertical portion 94*a* of the channel 94 has an open upper end. The restrictor 88 defines a concavity 88*a* and is movable within the vertical portion 94*a* from a retracted position in which the restrictor 88 is recessed within the channel 94 to an extended position in which the restrictor 88 projects from the open upper end of the channel 94. The restrictor 88 is biased to the extended position by a biasing member 116. In the extended position, the restrictor 88 is engaged with the wing 72 of the screw stop 70 to restrict movement of the screw stop 70 and, thus, movement of the drive screw 42.

The retention member 90 is received within the horizontal portion 94*b* of the channel 94 and is movable from a first position received within the concavity 88*a* of the restrictor 88 to retain the restrictor 88 in the retracted position to a second position spaced from the concavity 88*a* of the restrictor 88 to allow movement of the restrictor 88 from the retracted position to the extended position. In aspects of the disclosure, the retention member 90 includes a sphere and is biased towards the first position by a biasing member 120. Alternately, the retention member 90 can have a variety of configurations.

Figure 6:
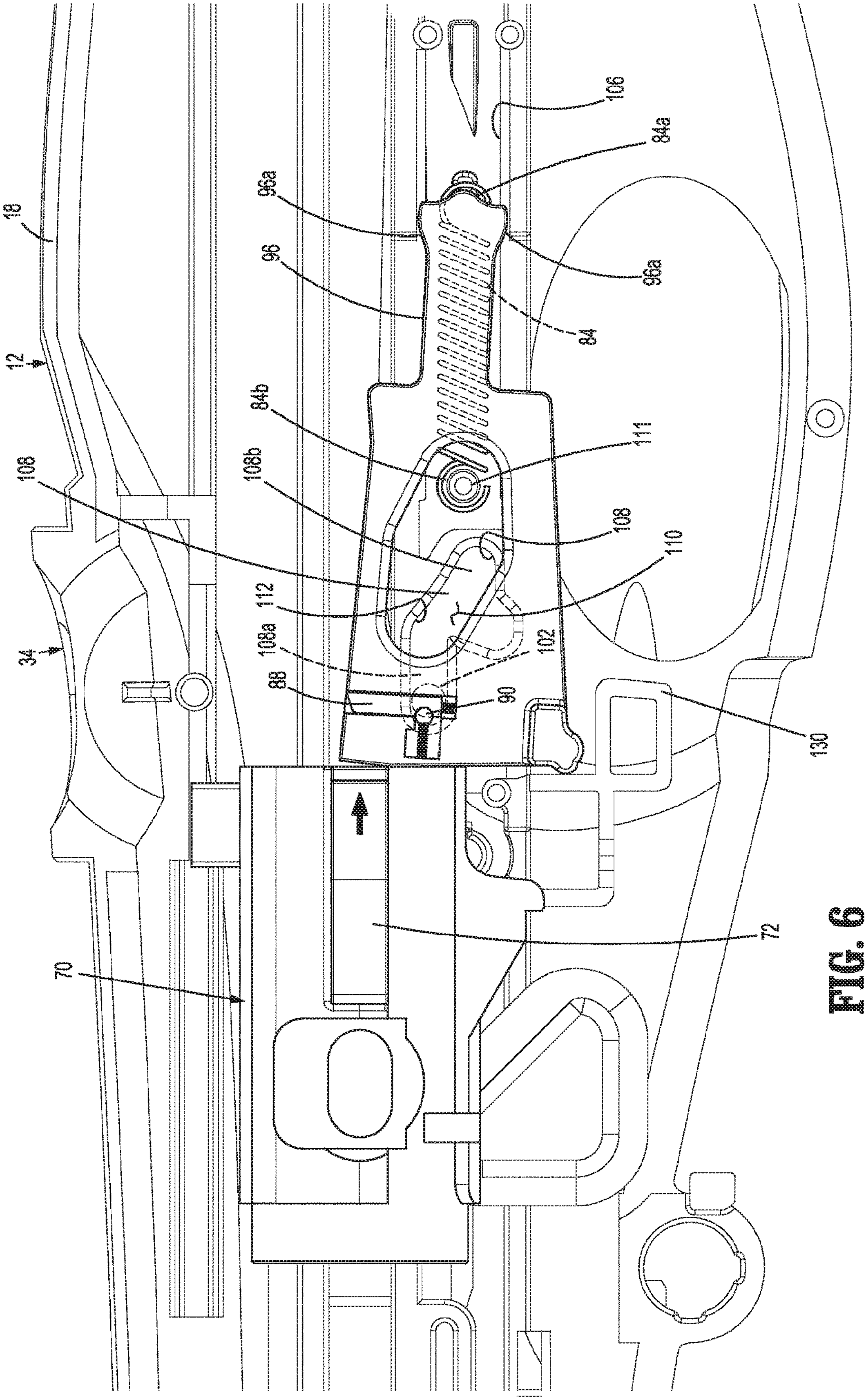
FIG. 6 is a side view of the portion of the handle assembly shown in FIG. 2 with a drive screw of the approximation mechanism removed and a screw stop of the approximation mechanism in a retracted position.

FIG. 6 illustrates the handle assembly 12 with the anvil assembly 20 in a clamped position (FIG. 1) after the stapling device 10 has been fired. In the clamped position, the drive screw 42 is in its proximal-most position and the screw stop 70 is positioned distally of the clicker 86. The clicker 86 is biased to its proximal-most position by the biasing member 84. In this position, the wing of the screw stop 70 is positioned slightly proximally of or in abutting relation to the proximal portion of the clicker 86.

Figure 7:
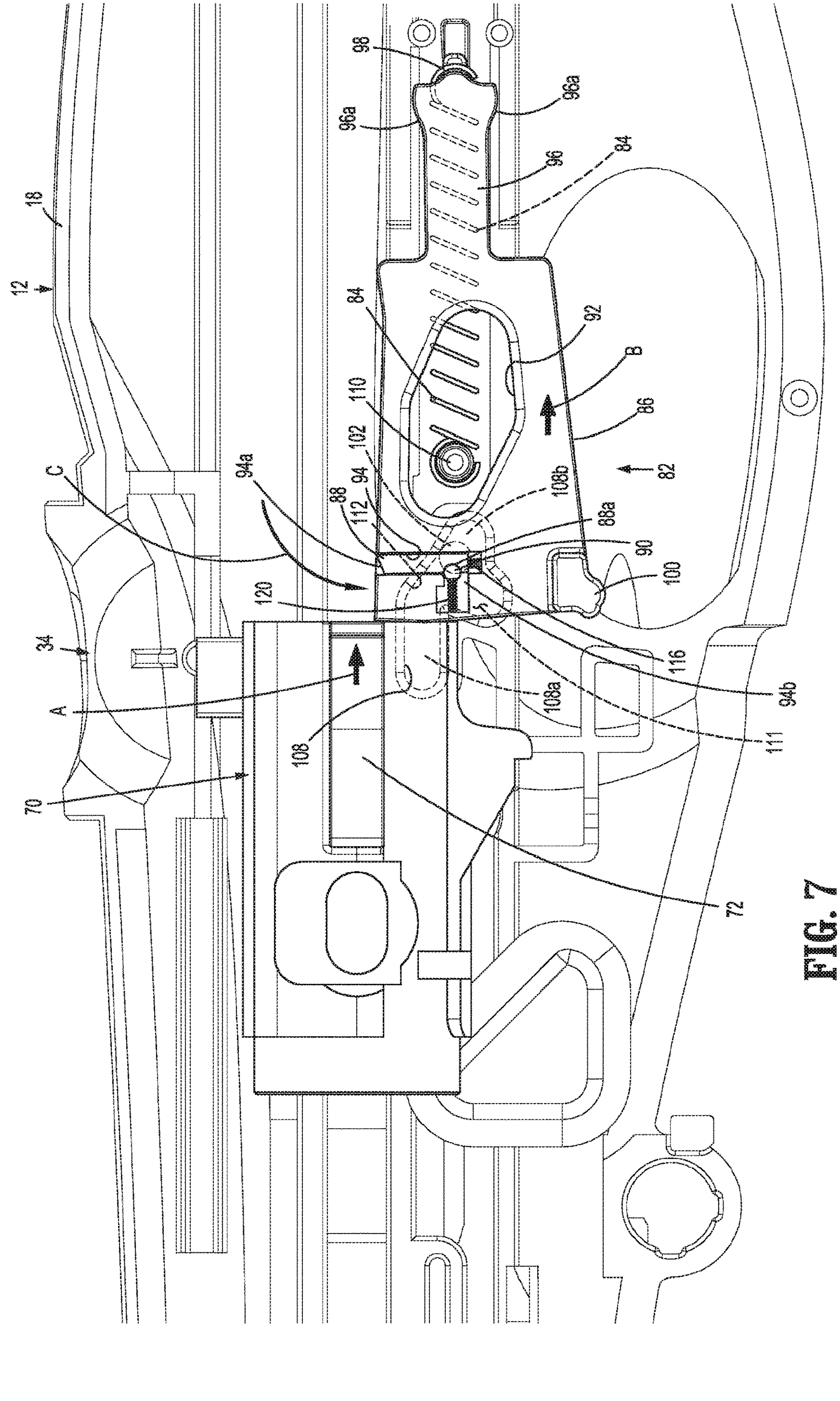
FIG. 7 a side view of the portion of the handle assembly shown in FIG. 6 as the approximation mechanism is actuated to move the anvil assembly from the clamped position towards the open position and to move screw stop into engagement with a clicker of the indicator assembly.

FIG. 7 illustrates the handle assembly 12 as the approximation mechanism 32 (FIG. 1A) is advanced to move the anvil assembly 20 from the clamped position (FIG. 1) towards the open position. When the approximation mechanism 32 is actuated by rotating the rotation knob 26 (FIG. 1), the drive screw 42 and the screw stop 70, which is secured to the drive screw 42, move proximally within the housing 18 of the handle assembly 12 in the direction of arrow "A" such that the wing 72 of the screw stop 70 engages the proximal end of the clicker 86 of the clicker assembly 82. As the screw stop 70 moves in the direction of arrow "A", the clicker 86 of the clicker assembly 82 is pushed distally in the direction of arrow "B" against the urging of the biasing member 84. As the clicker 86 moves in the direction of arrow "B", the boss 102 on the clicker 86 engages the cam surface 112 and is pressed downwardly to pivot the clicker 86 downwardly in the direction of arrow "c".

Figure 8:
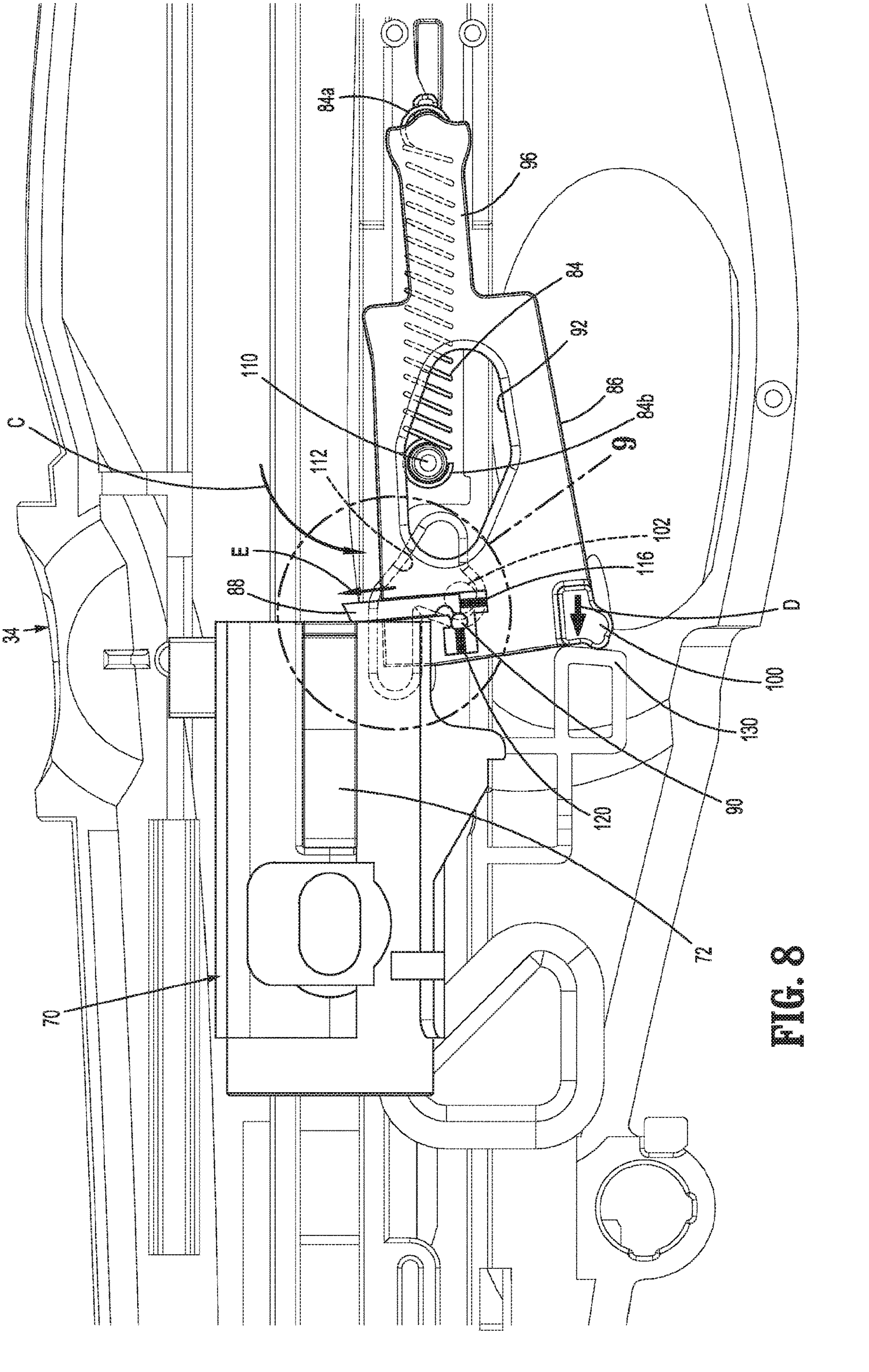
FIG. 8 a side view of the portion of the handle assembly shown in FIG. 7 as the approximation mechanism is actuated to move the anvil assembly towards the open position and move the clicker of the indicator assembly to an actuated position.
Figure 9:
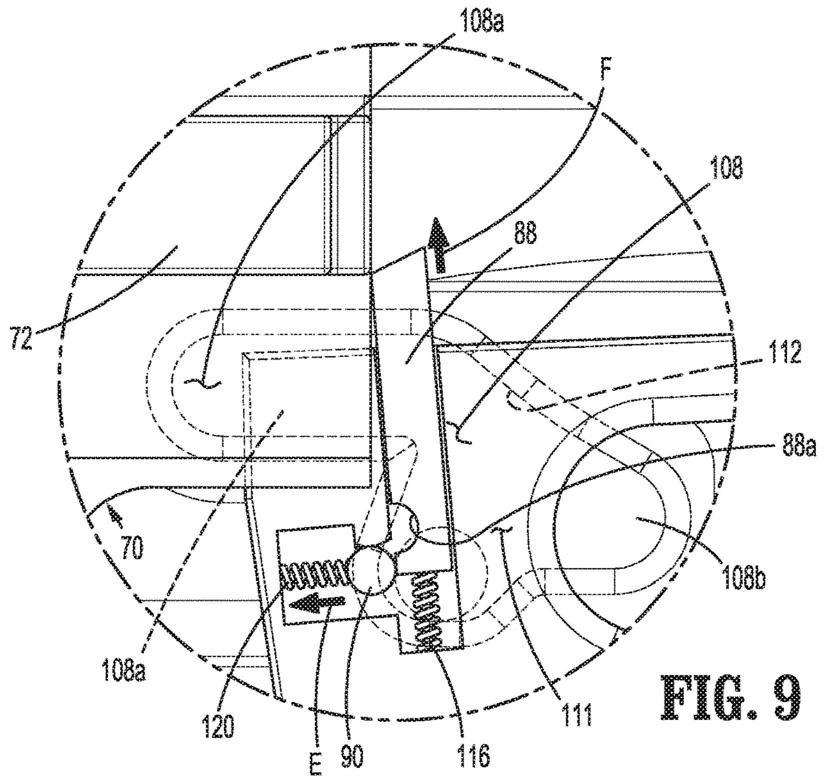
FIG. 9 is an enlarged view of the indicated area of detail shown in FIG. 8.

FIGS. 8-10 illustrate the handle assembly 12 as the approximation mechanism 32 (FIG. 1A) is advanced to a position in which the anvil assembly 20 is spaced from the reload assembly 18 (FIG. 1) a distance that is sufficient to allow the anvil head 56 (FIG. 10) to pivot from the operative position (FIG. 1) to the tilted reduced profile position. As the clicker 86 pivots downwardly in the direction of arrow "C", the clicker 86 moves downwardly past the wing 72 of the screw stop 70. When the clicker 86 passes below the wing 72 of the screw stop 70, the biasing member 84 snaps the clicker 86 proximally in the direction of arrow "D" such that the abutment member 100 engages an engagement surface 130 on the housing 18 of the handle assembly 12 (FIG. 1) to create an audible sound that indicates to a clinician that the anvil assembly 20 is spaced from the reload assembly 18 a distance sufficient to allow the anvil head 56 of the anvil assembly 20 to pivot to the tilted position.

When the clicker 86 moves in the direction of arrow "D" and the abutment member 100 engages the abutment surface 130 of the housing 18 of the handle assembly 12, the retention member 90 compresses the biasing member 120 and moves in the direction of arrow "E" from the concavity 88*a* of the restrictor 88. When this occurs, the biasing member 116 urges the restrictor 88 upwardly in the direction of arrow "F" into engagement with the wing 72 of the screw stop 70. This engagement between the restrictor 88 and the wing 72 increases resistance to movement on the screw stop 70 and on the approximation mechanism 32 that can be tactilely sensed by the clinician to further indicate to the clinician that the anvil head 56 has tilted and the stapling device 10 can be removed from the surgical site. In this position, the anvil assembly 20 is still locked onto the anvil retainer 46 and the anvil head is tilted.

Persons skilled in the art will understand that the devices and methods specifically described herein and illustrated in the accompanying drawings are non-limiting exemplary aspects of the disclosure. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A circular stapling device, comprising:

a handle assembly including a housing, a firing trigger, and an indicator assembly, the indicator assembly including a clicker assembly; and an elongate body having a proximal portion and a distal portion, the proximal portion coupled to the handle assembly;

a tool assembly coupled to the distal portion of the elongate body and including a reload assembly and an anvil assembly, the anvil assembly having a center rod and an anvil head, the anvil head coupled to the center rod for movement between an operative position and a tilted position; and an approximation mechanism including a rotation knob, a drive screw, a screw stop supported on the drive screw, and an anvil retainer, with:

the rotation knob rotatably supported on the housing of the handle assembly and coupled to the anvil retainer via the drive screw, the anvil retainer extending from the reload assembly and adapted to be releasably coupled to the center rod of the anvil assembly, the approximation mechanism being operable to move the anvil assembly in relation to the reload assembly between open and clamped positions;

wherein the clicker assembly comprises:

a clicker movable between a proximal position and a distal position in response to movement of the screw stop from a retracted position toward an advanced position; and a restrictor movable from a first position spaced from the screw stop to a second position engaged with the screw stop to increase resistance to movement of the screw stop, the increased resistance on the screw stop providing a tactile signal to a clinician that the anvil assembly is spaced from the reload assembly by a distance allowing movement of the anvil head from the operative position to the tilted position;

wherein movement of the clicker between its proximal position and its distal position in response to operation of the approximation mechanism provides an audible signal to the clinician that the anvil assembly is spaced from the reload assembly by the distance allowing the movement of the anvil head from the operative position to the tilted position.

2. The circular stapling device of claim 1, wherein the clicker includes an abutment member, and the housing of the handle assembly supports an engagement surface, the abutment member movable into engagement with the engagement surface when the clicker moves from its distal position towards its proximal position to provide the audible signal to a clinician.

3. The circular stapling device of claim 2, wherein the indicator assembly includes a biasing member that is positioned to urge the clicker assembly towards its proximal position.

4. The circular stapling device of claim 3, wherein the clicker supports a boss and the housing of the handle assembly defines a cam slot that receives the boss, the cam slot configured to pivot the clicker from a first position aligned with the screw stop to a second position misaligned with the screw stop in response to movement of the screw stop from its retracted position towards its advanced position.

5. The circular stapling device of claim 1, wherein the clicker defines a channel, and the restrictor is movable within the channel from the first position to the second position.

6. The circular stapling device of claim 5, wherein the clicker assembly includes a first biasing member that is positioned to urge the restrictor towards its second position.

7. The circular stapling device of claim 6, wherein the clicker assembly includes a retention member, the retention member engaging the restrictor to retain the restrictor in its first position.

8. The circular stapling device of claim 7, wherein the clicker assembly includes a second biasing member that is positioned to urge the retention member into engagement with the restrictor.

9. The circular stapling device of claim 8, wherein the channel includes a vertical portion and a horizontal portion, the restrictor received within the vertical portion of the channel and the retention member received within the horizontal portion of the channel.

10. A handle assembly comprising:

a housing defining a cavity and having an engagement surface;

an approximation mechanism including a rotation knob, a drive screw, and a screw stop supported within the housing on the drive screw, the screw stop movable between advanced and retracted positions within the housing in response to operation of the rotation knob; and an indicator assembly supported within the cavity of the housing, the indicator assembly including a clicker assembly, the clicker assembly including a clicker that is movable between a proximal position and a distal position in response to movement of the screw stop from a retracted position toward an advanced position, the clicker comprising:

an abutment member movable with the clicker from the distal position to the proximal position into engagement with the engagement surface of the housing in response to movement of the screw stop from its retracted position towards its advanced position to produce an audible signal; and a restrictor movable from a first position spaced from the screw stop to a second position engaged with the screw stop to increase resistance to movement of the screw stop within the housing of the handle assembly, the increased resistance on the screw stop providing a tactile signal.

11. The handle assembly of claim 10, wherein the indicator assembly includes a biasing member that is positioned to urge the clicker towards the proximal position.

12. The handle assembly of claim 11, wherein the clicker supports a boss and the housing of the handle assembly defines a cam slot that receives the boss, the cam slot configured to pivot the clicker in response to movement of the screw stop from its retracted position towards its advanced position from a first position aligned with the screw stop to a second position misaligned with the screw stop.

13. The handle assembly of claim 10, wherein the clicker defines a channel, and the restrictor is movable within the channel from the first position to the second position.

14. The handle assembly of claim 13, wherein the clicker assembly includes a retention member, the retention member engaging the restrictor to retain the restrictor in its first position.

15. The handle assembly of claim 14, wherein the clicker assembly includes a second biasing member that is positioned to urge the retention member into engagement with the restrictor.

16. The handle assembly of claim 15, wherein the channel includes a vertical portion and a horizontal portion, the restrictor received within the vertical portion of the channel and the retention member received within the horizontal portion of the channel.

* * * * *